United States Patent [19]

Stoy et al.

[11] Patent Number: 4,731,078
[45] Date of Patent: Mar. 15, 1988

[54] INTRAOCULAR LENS

[75] Inventors: Vladimir A. Stoy; George P. Stoy, both of Princeton, N.J.

[73] Assignee: Kingston Technologies Limited Partnership, Dayton, N.J.

[21] Appl. No.: 767,808

[22] Filed: Aug. 21, 1985

[51] Int. Cl.$^4$ .............................................. A61F 2/16
[52] U.S. Cl. ............................................................. 623/6
[58] Field of Search ................................................ 623/6

[56] References Cited

U.S. PATENT DOCUMENTS

| | | | |
|---|---|---|---|
| 3,034,403 | 5/1962 | Neefe | 351/160 R |
| 3,711,870 | 1/1973 | Deitrick | 623/6 |
| 3,760,045 | 9/1973 | Thiele et al. | 264/1 |
| 3,913,148 | 10/1975 | Potthast | 623/6 |
| 3,961,379 | 6/1976 | Highgate | 623/6 |
| 3,991,426 | 11/1976 | Flom et al. | 623/6 |
| 3,992,563 | 11/1976 | Tanaka | 526/219 |
| 4,037,929 | 7/1977 | Bricot et al. | 350/160 |
| 4,053,953 | 10/1977 | Flom et al. | 623/6 |
| 4,073,368 | 2/1978 | Levy, Jr. et al. | 623/6 |
| 4,110,848 | 9/1978 | Jensen | 623/6 |
| 4,131,604 | 12/1978 | Szycher | 528/79 |
| 4,153,641 | 5/1979 | Deichert et al. | 260/827 |
| 4,172,297 | 10/1979 | Schlegel | 623/6 |
| 4,198,714 | 4/1980 | Jensen | 623/6 |
| 4,206,518 | 6/1980 | Jardon et al. | 623/6 |
| 4,242,291 | 12/1980 | Hughes et al. | 264/1 |
| 4,244,060 | 1/1981 | Hoffer | 623/6 |
| 4,251,887 | 2/1981 | Anis | 623/6 |
| 4,253,199 | 3/1981 | Banko | 623/6 |
| 4,254,509 | 3/1981 | Tennant | 623/6 |
| 4,285,073 | 8/1981 | Szycher | 623/6 |
| 4,298,996 | 11/1981 | Barnet | 623/6 |
| 4,315,337 | 2/1982 | Choyce | 623/6 |
| 4,348,329 | 9/1982 | Chapman | 623/6 UX |
| 4,365,360 | 12/1982 | Ong | 623/6 |
| 4,373,218 | 2/1983 | Schachar | 623/6 |
| 4,377,329 | 3/1983 | Poler | 351/160 R |
| 4,466,705 | 8/1984 | Michelson | 350/418 |
| 4,512,040 | 4/1985 | McClure | 623/6 |
| 4,556,998 | 12/1985 | Siepser | 623/6 |
| 4,573,998 | 3/1986 | Mazzocco | 623/6 |
| 4,619,662 | 10/1986 | Juergens, Jr. | 623/6 |

FOREIGN PATENT DOCUMENTS 3428895  2/1986  Fed. Rep. of Germany .......... 623/6

Primary Examiner—Ronald L. Frinks
Attorney, Agent, or Firm—Alan M. Sack; Richard C. Woodbridge

[57] ABSTRACT

An artificial intraocular lens features an optical body for refracting images onto the retina and an outer surface that encloses the optical body, is exposed to fluid within the eye, and has a refractive index no greater than 1.40. In another aspect, the optical body includes an internal refractive surface whose contour can be selectively changed to change its refractive power.

26 Claims, 13 Drawing Figures

INTRAOCULAR LENS

BACKGROUND OF THE INVENTION

This invention relates to an artificial intraocular lens for insertion into the eye, for example to replace the natural lens after it has been removed because of injury or cataract.

A typical artificial intraocular lens (IOL) is fabricated of a clear, rigid, hydrophobic plastic material, usually polymethylmethacrylate (PMMA), to form an optical element with two curved faces. The IOL is typically implanted by inserting it via the same corneal or sclerotic incision used to remove the natural lens.

Conventionally, the IOL provides a single refractive power (for example, about +20 diopters) to focus images on the retina. The refractive power is determined by the relative indices of refraction of the eye's aqueous humor (1.34) and the lens material (1.50 in the case of PMMA) and the radii of curvature of the front and rear faces of the lens.

The IOL can be implanted either in the anterior chamber (located between the iris and cornea) or the posterior chamber (behind the iris). Because the IOL is typically both smaller and more dense than the natural lens, it must be held in place either by clipping it directly to the iris or suspending it by attachment fixtures, called haptics.

Various techniques have been proposed (a) to provide an IOL with a refraction power that can be changed to accommodate to distance or close-up viewing, (b) to render the IOL expandable to permit implantation of the contracted IOL via a small incision, and (c) to impart neutral buoyancy to the IOL.

SUMMARY OF THE INVENTION

The general feature of the invention is an IOL having an optical body that refracts images received via the cornea, and an outer surface that encloses the optical body, is exposed to fluid within the eye, and has a refractive index no greater than 1.40. The lens suppresses internal reflections and the refractive power of the lens can be made to be largely independent of the external configuration of the lens.

Preferred embodiments include the following features. The outer surface is a hydrogel polymer having an equilibrium water content of at least 65%, preferably at least 75%, most preferably at least 90%. The polymer is a hydrophilic derivative of polyacrylic or polymethacrylic acid, for example a copolymer containing hydrophilic and hydrophobic groups organized in continuous sequences. The hydrogel is covalently cross-linked. The outer surface includes ionized negatively charged groups. The optical body has an outer layer on which the outer surface lies, and an inner layer of different refractive index from the outer layer, the inner and outer layers meeting at an interface, refraction by the lens occurring primarily (e.g., more than 50%) at the interface.

The outer layer is a swellable material that has a gradient of swellability that decreases from a maximum value at the outer surface. The optical body has a plurality of layers comprising materials of different refractive index, the layers being defined by surfaces a plurality of which have the same radius of curvature. The optical body has an inner layer (e.g., fluid) having front and rear optical faces, and an outer layer enclosing the inner layer, the outer surface of said lens having front and rear exposed optical surfaces on the outer layer, the outer layer comprising two internal optical faces that respectively cooperate with the front and rear optical faces of the inner layer to define a pair of refractive interfaces, the inner and outer layers comprising materials of different refractive index. The fluid is a gas having a composition corresponding to the partial pressure of gases dissolved in the intraocular medium. At least one of the refractive interfaces is convex or concave, or is a Fresnel-like surface, or is planar.

In some embodiments, the contour of the outer surface, and the front-to-back thickness of the lens, are the same as for a natural lens. In some embodiments, the lens can be temporarily altered in shape to permit it to be inserted through a 4 mm² corneal incision. In some embodiments, the outer layer has a pair of fluid filled chambers located respectively in front of and behind the inner layer. The chambers are inflatable following implantation by absorption of water from the intraocular medium through the outer surface and into a dehydrated hydrophilic material in the chamber. In some embodiments, a rigid, resilient ring defines the perimeter of the optical body, the outer layer comprising a pair of films formed on and spaced apart by the ring, and the inner layer being defined between the respective internal faces of the films. There is a spacer peg having its ends in contact with the internal faces for resisting movement of the films toward each other caused by intraocular pressure. The peg is positioned on the optical axis of the eye.

In some embodiments, the optical body comprises means for imparting different selective refractive powers to the lens. The optical body has an enclosed chamber and the means for imparting includes fluids of different refractive index and a means for supplying volumes of the fluids to the chamber. When two fluids are used they are immiscible and of different density. One fluid is saline. The means for imparting includes a pair of layers within the optical body separated by a flexible interface, and a means for shifting the contour of the interface. The pair of layers comprise a chamber and the interface comprises a membrane that divides the chamber into two subchambers, and the means for shifting comprises a means for pumping selectable volumes of fluid into the subchambers. The pump comprises a membrane, and a magnet cooperating with the membrane, the magnet being positioned to interact with an external magnet placed in proximity to the cornea of the eye.

The lens has a central optical zone larger than 5 mm, a selective refractive power (when implanted) of between +5 and +30 diopters, a refractive index no greater than 1.35, a thickness before implantation between 0.2 and 1 mm and after implantation between 1 and 5 mm, a diameter of the optical portion between 6 and 9 mm, and a density between 0.95 and 1.05 (preferably between 0.98 and 1.02). The ratio of the lens refractive power in air to its refractive power when implanted is lower than 3, preferably lower than 1.5.

A second general feature of the invention is a lens in which the contour of an internal refractive surface is changed to change its refractive power.

Preferred embodiments include the following features. The internal refractive surface is a membrane separating two fluid-containing chambers and the fluid volumes or pressures are changed to switch the membrane from convex to concave. The fluids are supplied from two containers having flexible walls to change the fluid volumes in the two chambers. The flexible walls comprise a single membrane forming a common wall between the two containers. A magnet triggers the contour change. The contour of the outer surface of the lens is not affected.

The lens is collapsible and thus implantable with minimum trauma via a small incision, for example an incision as small as 4 mm$^2$. Once implanted, the lens is biocompatible with the intraocular medium, can fill the space occupied by the natural lens, permits diffusion of low molecular weight compounds, and can have the same density as the natural lens. Internal reflection and chromatic and spherical aberration are reduced. Refractive power in some embodiments can be changed easily. The Fresnel-like lens surface can be used without its sharp facets damaging the eye tissue. A wide variety of refractive powers can be achieved in a lens whose external shape and size is appropriate for implantation. The lens surface is gentle to surrounding tissue because the surface is highly hydrated, soft, and lubricious. When the density is identical to that of the intraocular medium, it may be possible to eliminate haptics. The refractive power can be obtained with a rigid, poorly biocompatible material and yet the lens can be foldable for insertion.

Other advantages and features will become apparent from the following description of the preferred embodiments, and from the claims.

DESCRIPTION OF THE PREFERRED EMBODIMENTS

We first briefly describe the drawings.

DRAWINGS

STRUCTURE AND OPERATION

Figure 1:
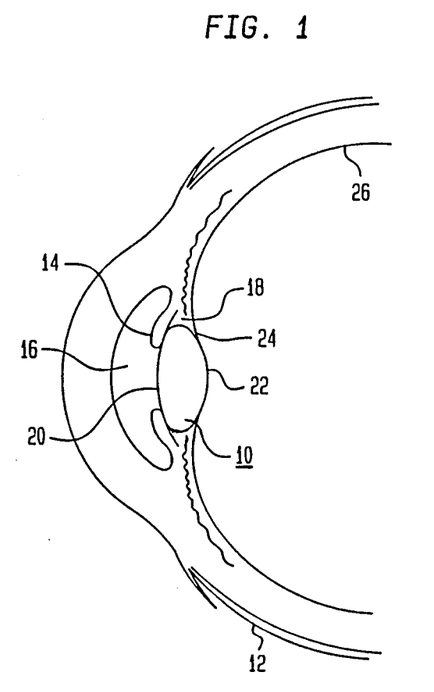
FIG. 1 is a sectional view of a portion of an eye.

Referring to FIG. 1, an artificial intraocular lens (IOL) 10 is implanted in an eye 12 is essentially the same position (behind iris 14 and anterior chamber 16 and within posterior chamber 18) where the removed natural lens was located. IOL 10 has a front surface 20 that forms an interface with iris 14 and with anterior chamber 16, and has a rear surface 22 that likewise forms an interface with the membrana hyaloidea 24 of vitreous body 26.

Figure 2:
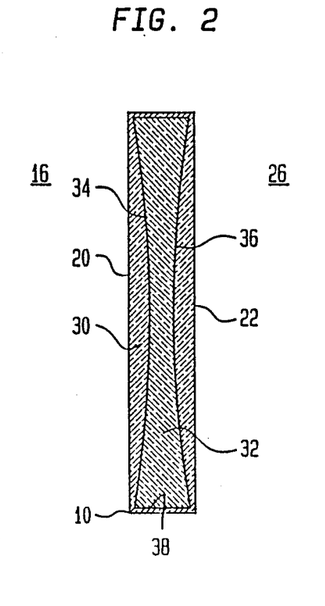
FIG. 2 is a schematic sectional view of an IOL.

IOL 10 can assume a variety of configurations not necessarily limited to the one suggested in FIG. 1. Referring to FIG. 2, IOL 10 has an optical body that includes outer and inner layers 30, 32, respectively. Outer layer 30 has a front face (outer surface) 20 in contact with the medium in anterior chamber 16 and a rear face 22 in contact with the medium in posterior chamber 26. Layer 32 is imbedded within layer 30 and has two interfaces 34, 36 with layer 30.

Layer 30 is formed of a hydrophilic hydrogel material with very high water content (more than 65%, preferably more than 75%, most preferably more than 90% water, in equilibrium) and a refractive index no greater than 1.40, preferably no greater than 1.35, most preferably 1.34 (the same as the refractive index of the aqueous humor in anterior chamber 16 and posterior chamber 26). The refractive power represented by the two faces 20, 22 is proportional to the difference in refractive indexes across those faces and is therefore small, preferably zero (i.e., when the refractive indexes of layer 30 and chambers 16, 26 are all equal).

Particularly preferred hydrogels for layer 30 are derivatives of polyacrylic or polymethacrylic acid, such as amides, carboxylates, and hydrophilic esters, and their mixtures, both covalently and physically cross linked. By amides are meant plain and also substituted acrylamide and methacrylamide. By carboxylates are meant salts of methacrylic and acrylic acid with inorganic and organic cations. By hydrophilic esters are meant acrylates and methacrylates of glycols, glycerine, sugars, saccharides, polysaccharides, polyethylenoxides, amino acids, amino alcohols, and the like.

Another preferred group of hydrogels for layer 30 are polymers and copolymers of hydrophilic vinyl derivatives such as 2-vinylpyrrolidone, vinylalcohol, vinyl sulfonic acid, or vinyl amine, which has a heteroatom in the side group (nitrogen, oxygen, or sulfur) bound directly to the carbon polymer backbone. Again, such compounds can be covalently or physically cross linked (see below).

Another possible group of hydrogels for layer 30 are copolymers containing long polyoxyethylene or polyethylene imine chains interconnected by means of suitable chemical bonds, particularly by urethane, urea, ester, ether, amide, or acetal bonds, for example, irradiation-cross linked polyethylenoxyde or hydrophilic segmented polyurethanes.

Another potentially useful group of hydrogels for layer 30 are polyelectrolyte complexes, which are mixtures of high-molecular polycations and polyanions, as described in Encyclopedia of Polymer Science and Technology, Vol. 10, page 765 (published by Interscience Publisher, 1968), incorporated herein by reference.

Also, the hydrogels for layer 30 can be modified natural polymers such as grafted polysaccharides, chemically substituted polysaccharides, modified polypetides, such as grafted and/or cross linked collagen, and their mixtures and combinations (for example, interpenetrating networks with synthetic hydrogels).

The choice of a suitable hydrogel for layer 30 is based, not only on its optical properties and water content, but also on its biocompatibility and chemical, photo- and mechanical stability, and its actual performance within the eye.

The covalent cross linking mentioned above in connection with any of the synthetic or natural hydrogels can be achieved by well known methods, for example, by reaction of side groups of the already made polymer with a bi- or polyfunctional reactive compound, or during polymerization by admixing a compound with two or more copolymerizable double bonds. Other possible cross linking techniques include polymerization of a monomer in a preformed lattice of basic polymer (interpenetrating networks), or cross linking by ionizing radiation.

Physical cross linking would be the result of specific attractive interaction between polymer chains or their parts, such as in already mentioned polyelectrolyte complexes. Alternatively, physical cross linking would be that of in grafted or block copolymers containing both hydrophilic and hydrophobic moieties organized in continuous sequences or blocks, which may be part of the basic chain (in block copolymers) or side chains (in grafted copolymers). Hydrophobic and hydrophilic moieties separate into two polymer phases, one being water-swellable and the other being non-swellable in water. The latter plays a role similar to that of chemical links in covalently cross linked hydrogels. If need be, both covalent and physical cross linking can be combined.

Examples of physically cross linked hydrogels for layer 30 may include polyurethanes with hydrophilic soft blocks and hydrophobic hard blocks, or partially hydrolyzed polyvinylacetates (i.e., block copolymers of vinylacetate and vinyl alcohol).

Particularly advantageous hydrogels are those based on modified polyacrylonitrile (PAN), which contains numerous sequences of PAN groups in each chain that alternate with sequences of hydrophilic derivatives of acrylic acid. Examples of such PAN derivatives are described in U.S. Pat. Nos. 4,331,783, 4,337,327, 4,369,294, 4,370,451, 4,379,874, and 4,420,589, incorporated herein by reference.

The advantage of hydrogels of the PAN derivative type are its excellent mechanical properties at very high water content, and the numerous types of functional groups which can be incorporated into their soft segments.

It is advantageous if at least surfaces 20, 22 of layer 30 contain ionized negatively charged groups, such as sulfo-groups, carboxylates, or sulphate groups. Surfaces containing such groups have excellent biocompatibility and extremely low friction with respect to adjacent tissue.

It is also advantageous to create a swelling gradient in layer 30, with swelling decreasing from its maximum value at interfaces 20, 22 inward. Such a gradient enables IOL 10 to merge into the intraocular medium 16, 26 with maximum physiological tolerance. The gradient can be achieved by assembling thin layers of hydrogels with gradually increasing swelling capacity, or possibly by introducing highly hydrophilic groups, such as ionized sulfo- or carboxylate groups, in gradually or continuously decreasing concentration from interfaces 20, 22 inward. The gradient can also be achieved, e.g., by chemical modification of the hydrogel outer layer, such as by sulfonation and/or sulphatation, which are diffusion controlled.

Another possibility is to create a gradient of composition and/or a gradient of network density (due to either covalent or physical cross linking) by well known methods.

The use of such a plurality of layers with different refractive index or a gradient of refractive index does not alter the refractive power of IOL 10 if the layers are parallel, i.e., if all interfaces between the layers have the same radii of curvature. Similarly, the sub-layers of material each with a constant refractive index in layer 30 all must have the same curvature to be optically inactive. Moderate deviations from this condition can be compensated by adjustments of curvature of the internal refractive interfaces 34, 36.

The gradient properties in layer 30 allow for maximum suppression of internal reflections and maximum utilization of ultra-high water content where it is the most important, i.e., at the IOL's interface with living tissues and intraocular medium.

Referring again to FIG. 2, the refractive power of IOL 10 is imparted almost solely (and preferably at least 50%) at the two interfaces 34, 36 across which there is a much larger difference in refractive index, than across faces 20, 22. The refractive power of IOL 10 depends both on this refractive index difference and on the respective radii of curvature of surfaces 34, 36, in accordance with the well-known equation $$1/f = D = \Delta n(1/R_1 + 1/R_2)$$

where f is the focal distance in meters, D is the refractive power in diopters, $\Delta n$ is the difference between the refractive indices, and $R_1$ and $R_2$ are the radii of curvature of the anterior and posterior surfaces (34, 36 in FIG. 2) of the inner layer respectively with respect to an incident beam. The refractive power of IOL 10, when implanted is between +5 and +30 diopters, depending on the configuration. The ratio of the refractive power in air to the refractive power, when implanted, is lower than 3, preferably lower than 1.5.

In FIG. 2, layer 32 is schematically depicted as being formed by a gas-filled biconvex cavity 38 in the shape of a conventional lens. Cavity 38 could also be plano-convex.

In the case where cavity 38 is filled with air (which has a refractive index of 1.00), $\Delta n$ is greater than or equal to 0.34, so that $R_1$ and $R_2$ in the above equation can be relatively large and the overall thickness of the lens can thus be relatively small while achieving high refractive power in a large diameter IOL 10. Furthermore, cavity 38 facilitates folding IOL 10 for implanting because IOL 10 can be relatively thin, gas is relatively flexible, surfaces 20, 22 can be flat, and two (or more) outer layers 30 can be bent or folded with relatively little stress.

Preferably cavity 38 is filled with a gas that is in thermodynamical equilibrium with gases dissolved in the intraocular medium, i.e., has a partial pressure corresponding to the partial pressure of gases dissolved in the intraocular medium.

Cavity 38 also could be filled with a low refractive index liquid, such as water, saline, aqueous solution of polymers, and the like. Then the overall lens thickness would be greater (depending on the refractive index of layer 30) because $\Delta n$ would be smaller than 0.34.

A broader range of materials can be used for layer 32 than for layer 30 because it is not in direct contact with living tissue. Essentially any material that has high clarity, is optically stable, and does not have leachable toxic and otherwise harmful impurities can be used.

For example, layer 32 could be polymers selected from hydrogels of the types listed for use in outer layer 30, with the same or lower water content.

Alternatively, layer 32 could be from the class of polyacrylates and polymethacrylates, such as polyacrylic and polymethacrylic esters of alcohols with one to eighteen carbons, and particularly with one to six carbons. Particularly advantageous would be polymers and copolymers of this type which are soft or flexible at body temperature, and more particularly covalently cross linked ones.

Other polymers for layer 32 can be polysiloxanes, polystyrene and its derivatives, polyacrylonitrile, polymers of vinyl derivatives, such as polyvinylcarbazole, polyvinyl pyrridine, polyvinylchloride, in various combinations of components, both plain and in combination with non-leachable plasticizers. Preferably the materials chosen for layer 32 will be flexible, although even rigid materials can be folded without a damage if in a thin layer (e.g., a thin membrane of polystyrene or polymethmetacrylate or even glass can be bent or folded without any destruction).

Thus even rigid materials and those with poor contact biocompatability can be used to produce a foldable, highly biocompatible IOL 10.

In any case, the combination of materials used for IOL 10 should be such that the overall density is equal to or very close to that of the intraocular medium, which is very close to 1.0, i.e., between 0.95 and 1.05, preferably between 0.98 and 1.02. This helps to diminish or even eliminate inertial forces (acceleration during head movements) which would tend to dislocate IOL 10, and may permit IOL 10 to be implanted without the need for haptics.

IOL 10 has a thickness prior to implantation of between 0.2 and 1 mm and after implantation between 1 and 5 mm. The optical portion of IOL 10 has a diameter between 6 and 9 mm.

Figure 3:
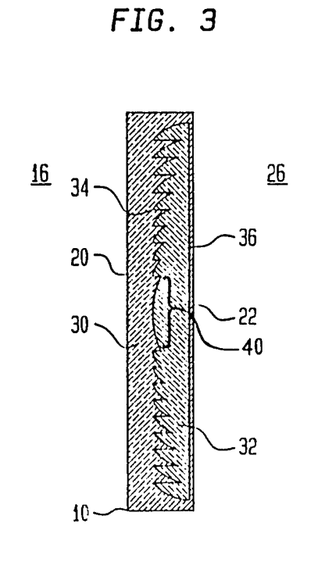
FIGS. 3, 4, 5A and 6, are sectional views of IOL embodiments.

Referring to FIG. 3, layer 32 could alternatively have a front interface 34 in the configuration of a modified Fresnel-like lens in which a central part 40 of the interface 34 has a conventional smoothly curved lens surface, while the remaining part has multiple facets.

The interface 34 represents the curved surface of an ordinary lens ("parent lens") disassembled in thin concentric strips (or a helix approximating such strips) and reassembled into a plane (or generally into any other surface different from the original surface). The normals to interface 34 as a function of distance from the optical axis approximate or are the same as in the parent lens and so are, therefore, the optical parameters. Thus the optical parameters and diameter of layer 32 are independent of its thickness and IOL 10 can have the shape of a thin foldable foil and yet have a large diameter, high refractive power, and small difference in refractive index.

The sharp edges of interface 34 are not in direct contact with intraocular medium or tissue.

A Fresnel-like interface 34 can be gas filled, or it can form the interface between a gas or liquid layer, and the neighboring polymer layer.

Interface 34 can be situated between two polymer layers with different refractive indexes, such as two layers of hydrogel with respectively different water content.

It is particularly advantageous to make continuously curved central part 40 with a diameter between 1 mm and 5 mm, which enables manufacture at much lower cost, and provides a central portion of IOL 10, utilized for focused (as opposed to peripheral) vision, which is undisturbed by the circular pattern of the remainder of interface 34.

The central portion 40 can be continuous because it does not contribute substantially to the overall thickness.

Figure 4:
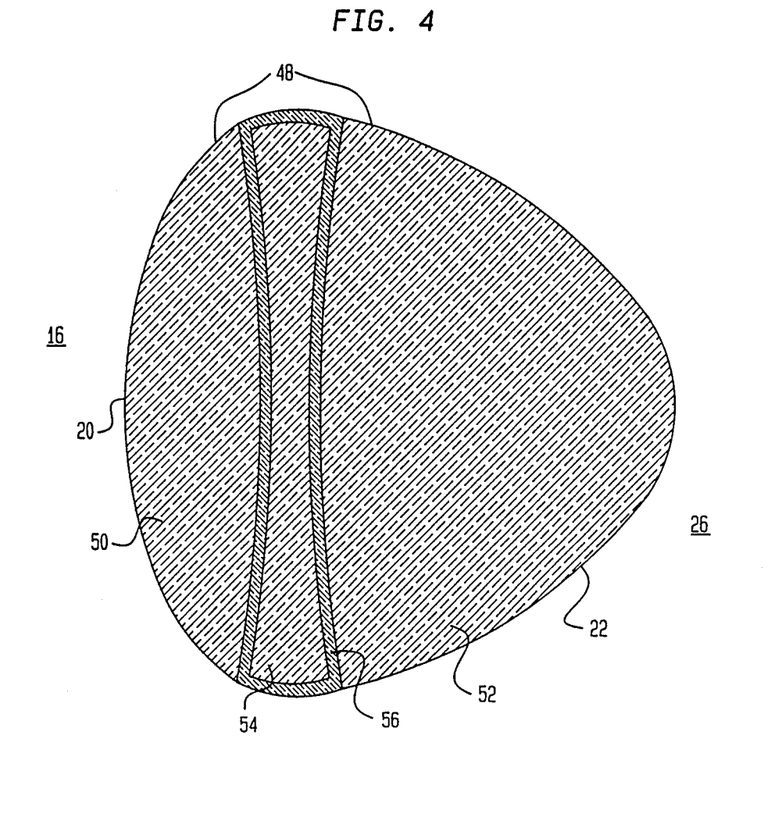

Referring to FIG. 4, in another embodiment the outer surfaces 20, 22 of IOL 10 can be curved with contours that simulate the contours of a natural lens. Surfaces 20, 22 are formed by a flexible membraneous skin 48 that defines the outer walls of front and rear chambers 50, 52 that can be inflated by filling with an essentially dry hydrophilic viscous aqueous solution (e.g., a solution of hyaluronic acid) having properties similar to the intraocular medium in chambers 16, 26, and molecular weight larger than the permeation limit of skin 48, so that inflation occurs automatically by water from the intraocular medium being absorbed through skin 48 into the dry hydrophilic polymer. Between chambers 50, 52 lies an air-filled cavity 54 within a hydrogel layer 56. Skin 48 is attached around the periphery of layer 56. The pressure differential across skin 48 is arranged to be zero or nearly zero. Refraction occurs only at the interfaces between layer 56 and cavity 54.

Figure 5A:
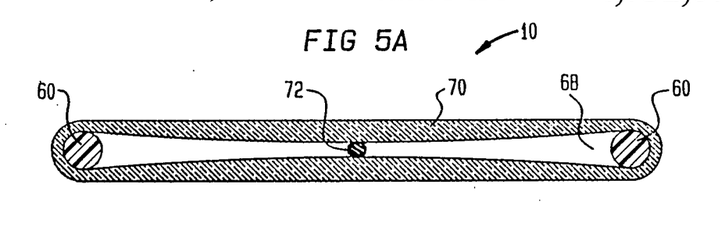
Figure 5B:
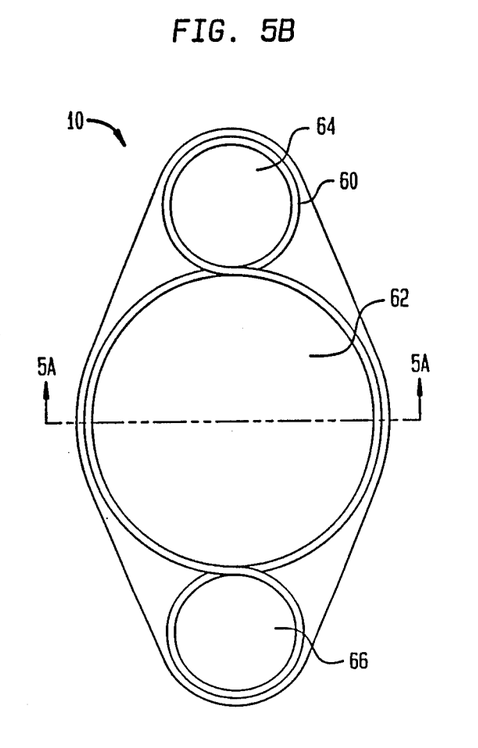
FIGS. 5B, 5C show front views of the IOL of FIG. 5A in respectively relaxed and extended positions.
Figure 5C:
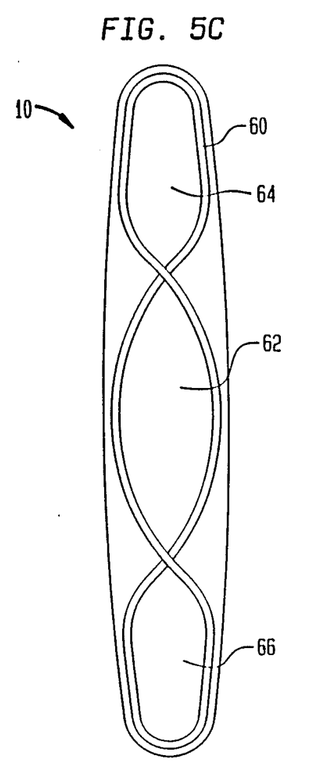

Referring to FIGS. 5A, 5B, in order to enable IOL 10 to resist intraocular pressure (typically 30 mm Hg) and at the same to permit easy insertion of IOL 10 through a small incision (e.g., as small as 4 mm$^2$), IOL 10 can be formed using a rigid flexible three-loop rim 60 which defines an optical portion 62 and two peripheral haptics 64, 66 for holding IOL 10 in place within the eye. Alternatively, rim 60 could have a single loop without haptics. Gas-filled cavity 68 is defined within a layer 70 of hydrogel elastic material (having refractive index near 1.34) that is stretched over and held in tension (like a drum) by rim 60, such that no part of rim 60 touches any living tissue of the eye. A spacer peg 72 at the optical axis (not shown in FIG. 5B) is connected to either or both adjacent walls (films) of layer 70 and aids in defining cavity 68 as against the intraocular pressure bearing on layer 70. Referring to FIG. 5C, in order to insert IOL 10 through a small corneal incision, rim 60 is deformed as shown; after insertion it returns to the configuration of FIG. 5B.

Figure 6:
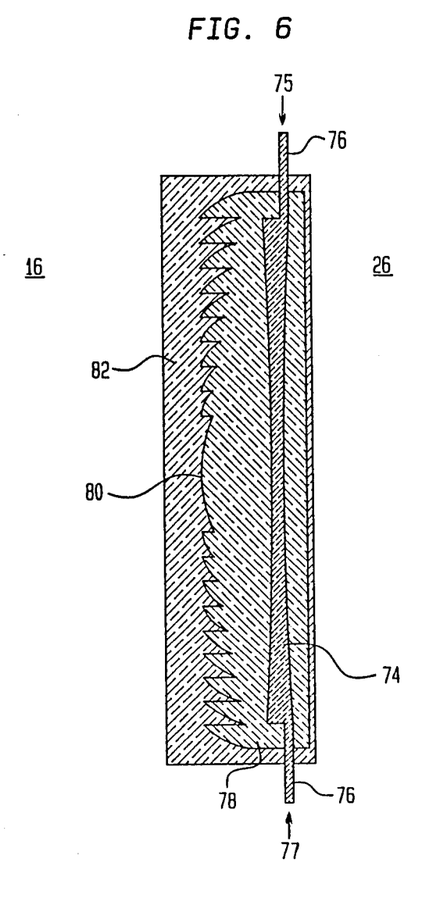

Referring to FIG. 6, IOL 10 can be structured to simulate the natural accommodation of the natural lens by changing the refractive power on demand between two dioptic values, for example, one corresponding to a long distance view and the other to a reading distance.

The change between the two refractive powers is achieved in an IOL 10 of the kind in which at least one internal layer is formed by a fluid medium.

The change of refractive power can be achieved either by a change of refractive index of the fluid medium, or by change of curvature of the interface between the fluid medium and the neighboring layer. A change of the refractive index can be achieved by exchanging one medium with another medium having a different refractive index, the media being preferably immiscible. For example, in FIG. 6, a layer 74 can be filled alternatively by two different fluids via channels 76 from a pair of supply chambers 75, 77. Because the interfaces between layers 74 and 78 have different curvatures, the contribution of layer 74 to the overall refractive power of IOL 10 will depend on its refractive index. A number of liquid pairs can be selected based on their immiscibility and different refractive indexes, e.g., water and bromobenzene.

An advantageous pair is saline and air since they are non-corrosive to many IOL materials, non-toxic, and have limited miscibility, a large difference in refractive index, and a large difference in density. The difference of refractive index is about 0.34. If the refractive index of layer 78 is, for example, 1.44, then the refractive power will be changed by a factor of $$0.44/0.1 = 4.4$$

If the refractive index of layer 78 is instead 1.35, then the refractive power will be changed by a factor of $$0.35/0.01 = 35$$

Thus, the refractive power can be readily changed in a broad dioptic range, particularly if combined with a refractive interface 80 of fixed optical power.

The refractive change is achieved by one medium (e.g., air) being fully replaced by another medium (e.g., saline) in layer 78. The medium exchange is facilitated by the difference of densities of the two media. In FIG. 6, 82 is the outermost hydrophilic layer with low refractive index, 78 is the inner layer with higher refractive index, and 80 is the refractive interface between layers 78, 82 in the form of a Fresnel-like lens.

The full replacement of medium can be also facilitated by including a thin flexible membrane 79 separating the media from each other in such a way that the membrane is closely adjacent to one or the other interface of layer 74. Being of uniform thickness, the membrane does not itself contribute to the overall refractive power of IOL 10. Such a membrane must be compatible with both fluids. It can be made, for instance, of silicone rubber, natural rubber, polyurethane, vinyliden chloride (Saran), polyethylene, or plasticized polyvinylchloride. The overall volume of layer 74 remains the same so that the channels 76 have to be connected to containers of variable volume, each containing one of the fluids and both preferably located outside the optical zone of IOL 10.

The change of the refractive power can be also achieved by changing the curvature of the interface between two of the layers having different refractive indexes. One approach is to have two layers formed by fluids, separated by a thin membrane which does not itself contribute to the refractive power. By changing volumes of the layers (the sum of their volume being constant) the separation membrane, and hence the interface, changes its curvature. For example, referring to FIGS. 7A, 7B, layers 93, 94 are chambers filled respectively with media of different refractive index, and a deformable membrane 95 forms a thin interface between them. The volumes of layers 93, 94 can be changed since they are connected to containers of variable volume (not shown) respectively via channels 96, 98. Membrane 95 can be made of a flexible material, and can be deformed into a spherical shape by a pressure differential between the layers 93, 94.

Figure 7A:
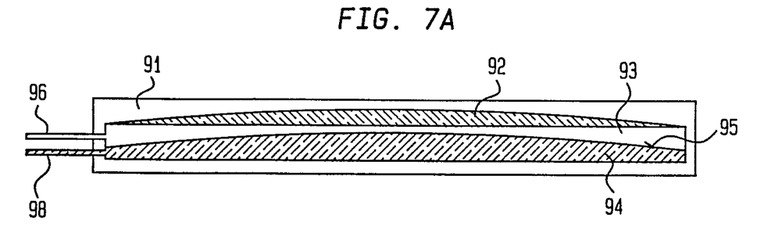
FIGS. 7A, 7B show schematic sectional views of an IOL embodiment with changeble refractive power.
Figure 7B:
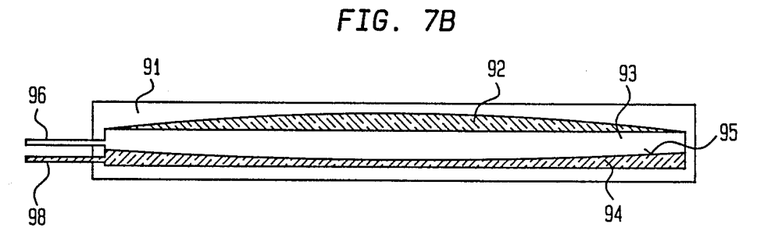

Finite changes in pressure (or volumes) in layers 93, 94 can cause finite changes in the shape of membrane 95, and thus in the refractive power of the interface. Such an arrangement could be utilized for continuous accommodation if the volume of the chambers could be derived from the tension in the ciliary muscles of the eye. The change of membrane geometry between two preset shapes can be achieved by changing the liquid volume adjacent to the membrane in exactly the preset increment.

In FIGS. 7A, 7B, outermost soft layer 91 has high water content and low refractive index; layer 92 has high refractive index and one convex interface; layer 93 is the layer of a fluid medium with very low refractive index, such as air; and layer 94 is the layer with a liquid medium with refractive index higher than that of layer 93. FIG. 7A shows the higher refractive state of IOL 10 with layer 95 convex (from direction of the incident beam). FIG. 7B shows the lower refractive power state with layer 95 concave.

Because the sum of the volumes of layers 93, 94 is constant, the media in layers 93, 94 should be supplied from separate containers subject to equal volume changes. If one medium is a gas, such as air, its supply container can have fixed volume but changing pressure.

Figure 8A:
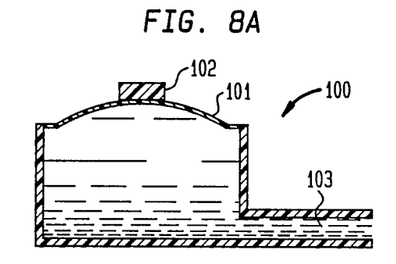
FIGS. 8A, 8B, 8C show schematic sectional side views of fluid chambers for supplying an IOL embodiment having a fluid cavity.
Figure 8B:
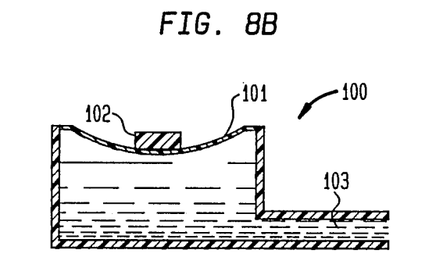
Figure 8C:
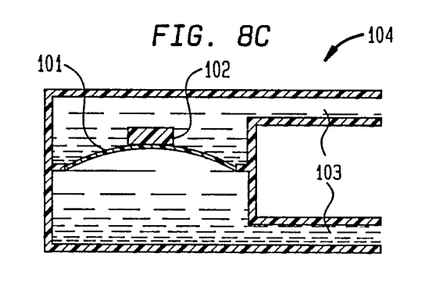

Referring to FIGS. 8A, 8B, 8C, a container 100 having a variable volume (where FIGS. 8A, 8B respectively show its configuration with its maximum and minimum volume) includes a deformable wall 101 formed by a bistable rigid membrane. The advantage of bistability is that the volume within container 100 can have only two stable values corresponding to volume changes in the corresponding layer in the IOL to which it is connected via a channel 103.

If variable volume containers are used to serve both media (which is advantageous in any case, and especially if both media are liquids) then it is advantageous to use an arrangement (FIG. 8C) where the bistable membrane 101 forms a partition wall between two compartments of a single container 104, the two compartments containing different media, assuring that the volume changes in both sides of membrane 104 are the same but of opposite signs. The pressure on membrane 101 operating to force the volume change is generated, for example, by permanent magnet elements 102 attached to membranes 101 with opposite polar orientation for containers 100 which contain the two media (in the case of FIGS. 8A, 8B). In the case of FIG. 8C a single magnetic element 102 suffices. The pressure can be generated by another magnet brought near to the outside the eye, which will push membrane 101, if seated in a convex position, into a concave position (if element 102 has the same polarity as the external magnet), or pull it from the concave position to the convex position if the polarities are opposite. The major advantages of direct magnetic action are that the magnetic field generates the necessary energy without an auxiliary power source (such as a battery); strong interference magnetic fields are rare; and no transducers or actuator elements are necessary. The same type of containers with variable volume and magnetic action can be used with the embodiments that involve changing the refractive index (i.e., exchange of two media in the same layer) or curvature of interface between two layers (membrane interface).

Other embodiments are within the following claims.

We claim:

1. An artificial intraocular lens for insertion into an eye comprising
    an optical body for placement across the optical axis of said eye for refracting images received via the cornea of said eye in order to focus said images on the retina of said eye,
    an outer surface that encloses said optical body and is exposed to fluid within said eye,
    said optical body comprising an outer layer on which said outer surface lies and an inner layer having an internal refractive surface, and
    means for selectively changing the refractive power of said internal refractive surface by changing the contour of said internal refractive surface.

2. The lens of claim 1 wherein said inner layer comprises
    a pair of chambers separated by a flexible membrane forming said internal refractive surface,
    said chamber respectively containing two fluids having different refractive indexes, and
    means for controlling said fluids to change said contour of said membrane.

3. The lens of claim 2 wherein
    said means for controlling comprises means for changing the volumes or pressures of said fluids in said chamber.

4. The lens of claim 1 wherein said internal refractive surface occupies a convex contour for one refractive power and occupies a concave contour for another refractive power.

5. The lens of claim 2 further comprising
two containers connected respectively to said chambers for holding supplies of said two fluids, each said container having a flexible wall, and
means for shifting the contour of each said flexible wall to change the volumes of said fluids in said chambers.

6. The lens of claim 5 wherein said flexible walls comprise a single membrane that forms a common wall between said two containers.

7. The lens of claim 2 wherein said means for controlling comprises a magnet for triggering said change of contour.

8. The lens of claim 1 wherein said contour is changed without changing the configuration of said outer surface.

9. An artificial intraocular lens for insertion into an eye comprising:
(a) an optical body for placement across the optical axis of said eye for refracting images received via the cornea of said eye in order to focus said images on the retina of said eye, said optical body including,
(i) an outer layer on which said outer surface lies, and
(ii) an inner layer of different refractive index from said outer layer, said inner and outer layers meeting at an interface more than 50% of the refraction by said lens occurring at said interface; and,
(b) an outer surface that encloses said optical body, is exposed to fluid within said eye and has a refractive index no greater than 1.40.

10. The lens of claim 9 wherein said outer layer comprises a swellable material having a gradient of swellability that decreases from a maximum value at said outer surface.

11. The lens of claim 9 wherein,
said inner layer has front and rear optical faces, said outer layer encloses said inner layer,
said outer surface of said lens comprises front and rear exposed optical surfaces on said outer layer, and
said outer layer comprises two internal optical faces that respectively cooperate with said front and rear optical faces of said inner layer to define a pair of refractive interfaces.

12. The lens of claim 11 wherein at least one of said refractive interface is convex or concave.

13. The lens of claim 11 wherein said refractive interface is planar.

14. The lens of claim 11 further comprising a rigid, resilient ring for defining the perimeter of said optical body,
said outer layer comprising a pair of films formed on and spaced part by said ring, and
said inner layer being defined between the respective internal faces of said films.

15. The lens of claim 14 further comprising a spacer peg having its ends in contact with said internal faces for resisting movement of said films toward each other caused by intraocular pressure.

16. The lens of claim 15 wherein said peg is positioned on the optical axis of said eye.

17. The lens of claim 9 wherein said inner layer comprises a fluid.

18. The lens of claim 17 wherein said fluid is a gas having a composition corresponding to the partial pressure of gases dissolved in the intraocular medium.

19. The lens of claim 9 wherein said interface comprises a Fresnel-like surface.

20. The lens of claim 9 wherein said outer layer comprises a pair of fluid filled chambers located respectively in front of and behind said inner layer, at least one said chamber being filled by a viscous, water heavy material.

21. The lens of claim 20 wherein said chambers are inflatable following implantation.

22. The lens of claim 21 wherein said chambers comprise a dehydrated hydrophilic material not permeable through said outer surface, and said inflation occurs by absorption of water from the intraocular medium in said eye, through said outer surface, and into said hydrophilic material.

23. An artificial intraocular lens for insertion into an eye comprising;
(a) an optical body for placement across the optical axis of said eye for refracting images received via the cornea of said eye in order to focus said images on the retina of said eye, said optical body includes,
(i) a plurality of layers, said layers comprising materials of different refractive index, said layers being defined by surfaces, a plurality of which have the same radius of curvature;
and,
(b) an outer surface that encloses said optical body, is exposed to fluid within said eye and has a refractive index no greater than 1.40.

24. An artificial intraocular lens for insertion into an eye comprising:
(a) an optical body for placement across the optical axis of said eye for refracting images received via the cornea of said eye in order to focus said images on the retina of said eye, said optical body includes means for imparting different selective refractive powers to said lens, including,
(i) a pair of layers within said optical body separated by a flexible interface, and
(ii) means for shifting the contour of said interface; and,
(b) an outer surface that encloses said optical body, is exposed to fluid within said eye and has a refractive index no greater than 1.40.

25. The lens of claim 24 wherein
said pair of layers comprise a chamber and said interface comprises a membrane that divides said chamber into two subchambers, and
said means for shifting comprises means for pumping selectable volumes of fluid into said subchambers.

26. An artificial intraocular lens for insertion into an eye comprising:
(a) an optical body for placement across the optical axis of eye for refracting images received via the cornea of said eye in order to focus said images on the retina of said eye, said optical body includes,
(i) a chamber, and
(ii) means for imparting different selective refractive powers to said lens including a pump for delivering fluid into said chamber said pump comprises a membrane, a magnet cooperating with said membrane, said magnet being positioned to interact with and external magnet placed in proximity to the cornea of said eye; and, (b) an outer surface that encloses said optical body, is exposed to fluid within said eye and has a refractive index no greater than 1.40.

* * * * *